United States Patent
Strandqvist

(10) Patent No.: US 6,930,221 B1
(45) Date of Patent: Aug. 16, 2005

(54) ABSORBENT STRUCTURE HAVING IMPROVED ABSORPTION PROPERTIES

(75) Inventor: Kersti Strandqvist, Pixbo (SE)

(73) Assignee: SCA Hygiene Products AB, Gothenburg (SE)

( * ) Notice: Subject to any disclaimer, the term of this patent is extended or adjusted under 35 U.S.C. 154(b) by 362 days.

(21) Appl. No.: 09/699,451

(22) Filed: Oct. 31, 2000

Related U.S. Application Data

(63) Continuation of application No. PCT/SE99/00627, filed on Apr. 20, 1999.

(30) Foreign Application Priority Data

Apr. 28, 1998 (SE) .................................. 9801490

(51) Int. Cl.[7] .............................................. A61F 13/15
(52) U.S. Cl. ...................................... 604/365; 604/367
(58) Field of Search ................................ 604/367–369

(56) References Cited

U.S. PATENT DOCUMENTS

| | | | |
|---|---|---|---|
| 3,901,236 A * | 8/1975 | Assarsson et al. | 604/368 |
| 5,126,382 A * | 6/1992 | Hollenberg | 524/56 |
| 5,328,939 A * | 7/1994 | Smith | 521/187 |
| 5,382,610 A * | 1/1995 | Harada et al. | 524/35 |
| 5,384,343 A * | 1/1995 | Farrar et al. | 523/129 |
| 5,607,414 A * | 3/1997 | Richards et al. | 604/378 |
| 5,684,106 A * | 11/1997 | Johnson et al. | 526/295 |
| 5,702,381 A * | 12/1997 | Cottenden | 604/385.01 |
| 5,957,203 A * | 9/1999 | Hutchins et al. | 166/295 |
| 6,376,034 B1 * | 4/2002 | Brander | 428/35.2 |
| 6,455,600 B1 * | 9/2002 | Hahnle et al. | 521/63 |

* cited by examiner

Primary Examiner—Larry I. Schwartz
Assistant Examiner—C. Lynne Anderson
(74) Attorney, Agent, or Firm—Young & Thompson

(57) ABSTRACT

An absorbent structure in an absorbent article such as a diaper, a pant diaper, an incontinence guard, a sanitary napkin or the like, includes a combination of a porous material such as fibers and/or foam, and at least 50% by weight of a superabsorbent material in at least one area thereof in which the superabsorbent material is distributed. The superabsorbent material is cross-linked by ionic bonds, preferably a polyvalent metal ion. The superabsorbent may further be covalently cross-linked.

9 Claims, 4 Drawing Sheets

ABSORBENT STRUCTURE HAVING IMPROVED ABSORPTION PROPERTIES

This application is a continuation of international application PCT/SE99/00627 filed Apr. 20, 1999, which claims the priority of Swedish application 9801490-5 filed Apr. 28, 1998.

TECHNICAL FIELD

The present invention refers to an absorbent structure in an absorbent article such as a diaper, a pant diaper, an incontinence guard, a sanitary napkin or the like, said structure comprising a combination of a porous material such as fibers and/or foam, and superabsorbent material. The invention also refers to an absorbent article containing such an absorbent structure.

BACKGROUND OF THE INVENTION

For absorbent articles of the above mentioned kind it is of essential importance that they have the ability to quickly receive and absorb large amounts of liquid. It is further of importance that liquid can be distributed from the wetting area to other parts of the absorbent structure, so that the total absorption capacity of the article can be utlilized.

It is further essential that the absorbent structure can retain the liquid also when exerted to external loadings, such as when the user is moving, is sitting or lying down.

One problem, especially for diapers and incontinence guards, which are intended to receive and absorb relatively large amounts of liquids, is that they risk to leak before their total absorption capacity is fully utilized. A reason for such a leakage is that the absorbent structure, especially at repeated wettings, has a decreased capacity to quickly receive and absorb large amounts of liquid.

Absorbent articles of this kind comprise a liquid pervious topsheet, a liquid impervious backsheet and an absorbent structure arranged therebetween, said absorbent structure comprising a liquid acquisition layer located adjacent the liquid pervious topsheet, and one and more liquid storage and liquid distribution layers.

In order to obtain a high absorption capacity and a high liquid retaining capacity when the article is exerted to outer loadings it often contains so called superabsorbents. Superabsorbents are crosslinked polymers with capacity to absorb liquid in an amount several times, 10 times or more, their own weight. They further have the capacity to retain absorbed liquid also when exerted to an external pressure. They have gained wide use in absorbent articles, at which they usually are in particulate form, such as grains, granules, flakes or fibers and they are mixed or layered with other absorption materials, usually cellulosic fibers.

The efficiency of a superabsorbent is dependant on many factors, such as where and how the superabsorbent is mixed into the absorbent structure, what physical shape the superabsorbent particles have, and the properties of the superabsobent such as absorption rate, gel strength and liquid retaining capacity.

An important reason that the absorbent structure functions unsatisfactory at repeated wettings, i e at the second and third wetting occasions, is that it is difficult for the superabsorbent material to maintain its structure and shape after the superabsorbent particles have swollen. The firmness and shape of the superabsorbent particles can for example be weakened at outer loadings. By the fact that a superabsorbent at external loadings and after the first and second wetting has difficulty to maintain its structure and shape, a common phenomena called gelblocking occurs. Gelblocking means that the superabsorbent when wetted forms a gel which blocks the pores in the porous fiber structure and by that detonates the liquid transport from the wetting area to other parts of the absorbent structure. This involves that the total absoption capacity of the absorbent structure is not optimally utilized, and also involves an increased risk for leakage.

The problem of gelblocking increases when the amount of superabsorbent material in an absorbent structure is high. In order to make an article that is discrete and comfortable to wear it is however a desire that the article is thin. In order to maintain a high liquid absorption capacity such thin articles often have a relativley high amount of superabsorbent material.

In order to improve the capacity of the superabsorbent to maintain its structure even at an outer loading and after a plurality of wettings the superabsorbent material is often crosslinked in two steps. The first crosslinking is a so called internal crosslinking and is made by copolymerization of acrylic acid and at least one bifunctional agent under the formation of a network.

Copolymerizeable crosslinking agents used in superabsorbent polymers usually consist of bifunctional substances such as diacrylate esters and allylmethacrylates of trifunctional substances such as 1,1,1-trimethylol propane triacrylate and triallylamine or of tetra-functional substances such as tetraallyloxyethane.

The second crosslinking is a so called surface crosslinking and involves that the superabsorbent easier maintains its original shape also when exerted to external loads and after several wettings. Surface crosslinking of the superabsorbent is usually made by esterification of carboxylic groups. One example of surface crosslinking agents are polyhydroxy substances. Another example is organic carbonates, preferably ethylene carbonate in acqeous solution. A third example is the use of diglycidyl compounds, especially ethylene glycol-diglycidylether (EDGE).

It is also known through e g U.S. Pat. No. 4,043,952 to surface crosslink a superabsorbent based on an anionic polyelctrolyte with a polyvalent metal ion, for example aluminum. The surface crosslinking occurs with ionic bonds. It is stated that the superabsorbent in question has an improved dispersability in an acqeous medium. There is no mentioning about an effect on the absorption capacity in an absorbent article.

Through EP-B-0 248 963 it is known to surface crosslink a superabsorbent of anionic character with a polyquartenary amine for increasing the absorption capacity of the superabsorbent. Also here the crosslinking is made by means of ionic bonding.

THE OBJECT AND MOST IMPORTANT FEATURES OF THE INVENTION

The object of the present invention is to provide an absorbent structure in an absorbent article of the above mentioned kind and which contains a high amount of superabsorbent material, said absorbent structure having improved properties with respect to liquid acquisition capacity and distribution capacity at repeated wettings. This has according to the invention been achieved by the fact that the absorbent structure contains at least 50% by weight superabsorbent material, based on the total weight of the structure in dry condition in at least one area thereof in which the superabsorbent material is distributed, said superabsorbent material is crosslinked by means of ionic bonds.

The superabsorbent material can also be covalently crosslinked by means of another crosslinking agent.

The superabsorbent material preferably comprises a polymer with anionic functional groups, for example a crosslinked polymer of a polyacrylate having functional carboxy groups.

The superabsorbent material is preferably crosslinked by cations, which by means of ionic bonds are bonded to the anionic functional groups of the superabsorbent material. According to one embodiment, the cationic crosslinking agent comprises a polyvalent metal ion, for example aluminum, zirconium, chrome, titanium or zinc. According to a preferred embodiment, the ionic crosslinking is made by aluminate ions, $[Al(OH)_4]^-$.

The superabsorbent material can either be surface crosslinked by the ionic crosslinker or substantially homogeneously crosslinked therewith.

According to one embodiment the absorbent structure contains at least 70% by weight superabsorbent material, based on the total weight of the structure in dry condition in at least one area in which the superabsorbent material is distributed.

The invention further refers to an absorbent article such as a diaper, a pant diaper, an incontinence guard, a sanitary napkin or the like comprising a liquid pervious topsheet, a liquid impervious backsheet and an absorbent structure arranged therebetween, at which the absorbent structure is of the kind stated above.

DESCRIPTION OF DRAWINGS

The invention will in the following be closer described with reference to the accompanying drawings.

DESCRIPTION OF EMBODIMENTS

Figure 1A:
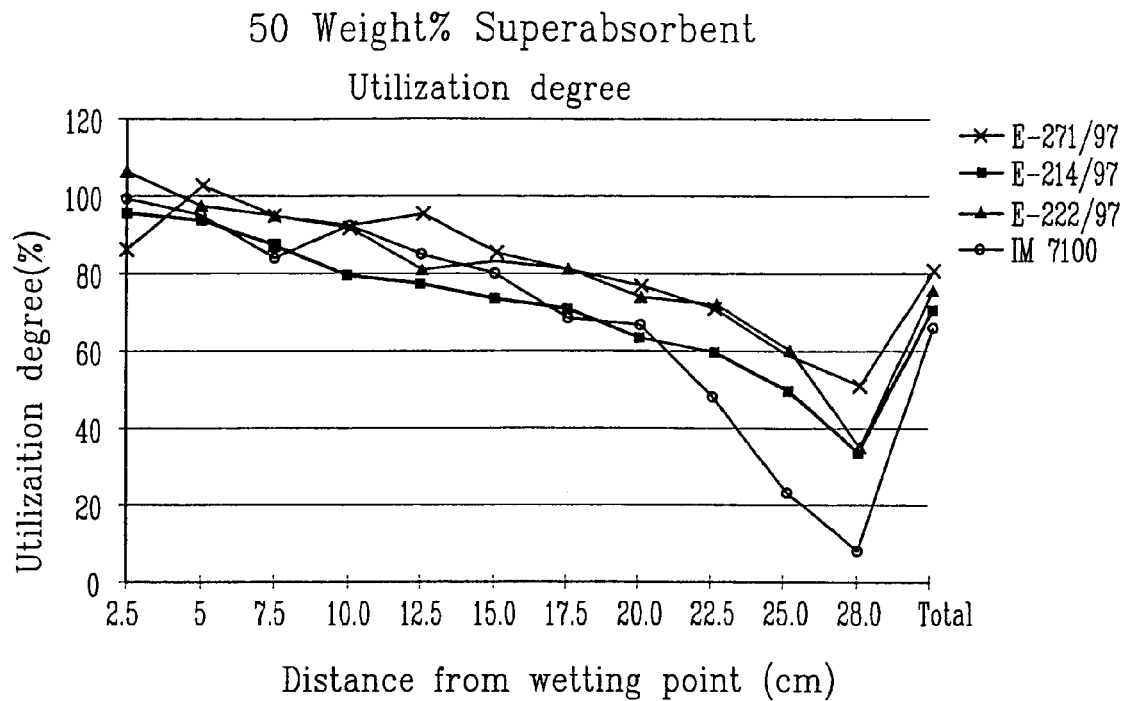
FIGS. 1a and b show in the form of diagrams a comparison of the utilization degree of the absorption capacity of an absorbent article on different distances from the wetting area and where the article contains different superabsorbents in an amount of 50 and 70% by weight respetively.
Figure 1B:
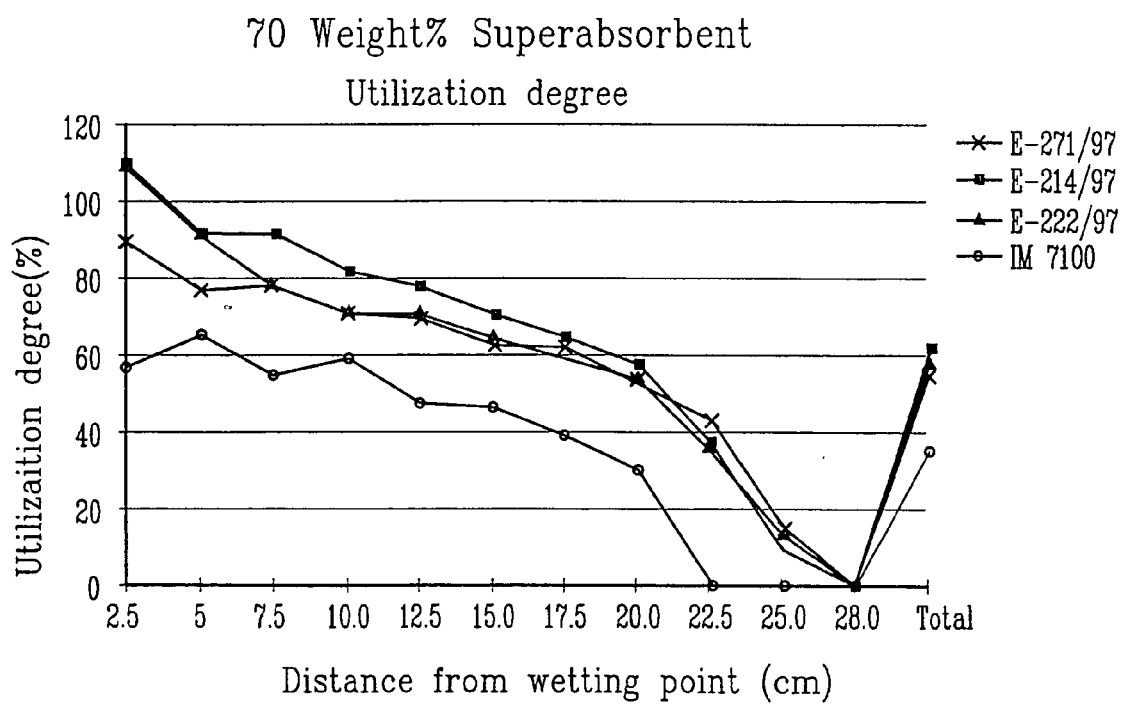

Superabsorbent materials are defined as such materials that under gel formation can absorb many times their own weight, 10 times or more, of body liquids and test liquids comparable thereto such as synthetic urine or 0.9% saline solution. Such materials may e g be hydrogel-forming polymers in the form of alkali salts of polyacrylic acid, polymethacrylic acid, copolymers of acrylic- and methacrylic acid with other monomers, acrylic acid grafted starch, polysaccharides such as carboxymethyl starch, carboxymethyl cellulose, xanthane, alginate, chitosane, pectine, guar gum, and peptides and proteins etc. The hydrogel forming polymers are usually crosslinked for making them water insoluble. Commonly used crosslinkers are ethylene glycol dimethacrylate, diethylene glycol diacrylate, allylmethacrylate, 1,1,1-trimethylolpropane triacrylate, triallyamine and tetraallyl oxyethane, which are bonded to the polymeric structure by means of covalent bonds.

According to the invention the superabsorbent is surface crosslinked or homogeneously crosslinked by a polyvalent crosslinking agent by means of ionic bonds. Besides it is preferably also covalently crosslinked by another crosslinking agent. The superabsorbent material preferably comprises a polymer with anionic functional groups such as carboxy groups, sulphonate groups, sulphate groups, phosphate groups, amide groups or nitrile groups, preferably however carboxy groups. The ionic crosslinking agent consists of cation, which by ionic bonds are bonded to the anionic functional groups of the superabsorbent material. The cation preferably comprises a polyvalent metal ion such as aluminum, zirconium, chrome, titanium or zinc.

Preferably, the crosslinking agent is an aluminate ion, $[Al(OH)^4]^-$ in accordance with what is disclosed in the German patent application no. 198-18852.8 filed the same day. When producing such a superabsorbent, aluminate ions are added to a water-containing gel of a carboxy group containing polymer, e.g., a polyacrylate, which preferably is crosslinked by means of covalent bonds in a conventional way. The gel is crosslinked with the aluminate ions before drying to a powder or granules, at which a homogeneously ionically crosslinked hydrogel structure is obtained.

When a superabsorbent absorbs liquid and swells, the covalent bonds to the crosslinking agent are successively broken up, which leads to that the superabsorbent loses its gel stability in connection with the swelling. A superabsorbent, however, which is surface crosslinked or homogeneously crosslinked by an ionic crosslinking agent, maintains its gel stability after swelling in a better way, due to that the ionic bonds can be rearranged and recreated as the polymer swells, which a covalent bond is not able to do.

The superabsorbent according to the present invention can thus be both covalently and ionically crosslinked, or only ionically crosslinked. The ionic crosslinking can either be on the surface of the superabsorbent particles or homogeneously through the entire structure of the superabsorbent.

The porous structure in which the superabsorbent is contained can be of optional kind, such as a fibrous structure of cellulosic fluff pulp, synthetic fibers of different kind, regenererated cellulosic fibers or mixtures thereof. The porous structure can also consist of an absorbent foam material.

The superabsorbent can either be mixed with the porous structure or be applied as a layer therein. Is is also possible to apply a layer of superabsorbent material between two layers of porous material.

The amount of superabsorbent material in the absorbent structure should be at least 50% by weight calculated on the weight of the structure in dry condition in at least one area in which the superabsorbent material is distributed. This means that in for example a double- or multilayered structure with different amounts of superabsorbent material in the different layers, the amount of superabsorbent material should be at least 50% by weight in at least one of the layers. The total amount of superabsorbent material in the entire absorbent structure, however, could be lower than 50% by weight.

According to one embodiment the amount of superabsorbent material in the absorbent structure should be at least 70% by weight calculated on the weight of the structure in dry condition in at least one area in which the superabsorbent material is distributed. The physical shape of the superabsorbent material is important for its function in the absorbent structure and is preferably in the form of a powder, grains or granules. Below a number of tests are disclosed which were made with respect to utilization degree, acquisition time and rewet in absorbent structures containing a combination of pulp fibers (chemical pulp) and 50 and 70% by weight respectively of a superabsorbent material of four different types. The test absorbent bodies were of the size 28×10 cm, with a surface weight of 300 g/m² and a bulk of 3 cm³/g. The superabsorbent particles were substantially homogeneously mixed with the pulp fibers.

The superabsorbents that were used were a commercially available superabsorbent from Clariant GmbH named Sanwet IM 7100 and three different test substances of a polyacrylate homogeneously crosslinked by aluminate ions according to above and which besides was covalently crosslinked. The test substances were named E271/97, E214/97 and E222/97 and were supplied by Clariant GmbH and Clariant Corp.

Utilization Degree

The absorbent bodies were placed with an inclination of 30° in order to imitate the placing of the diaper during use. The lower end was in contact with a liquid bath of synthetic urine (formula according to below) and was allowed to suck liquid during 60 minutes. The length of the wet area was measured. Test bodies were cut in smaller pieces corresponding to different lengths and were weighed. The utilization degree was calculated according to the formula:

Utilization degree=Absorbed weight of urine (g)/
Theoretical absorption capacity (g), at which
Absorbed weight of urine=Weight of the sample after absorption−Dry weight;
Theoretical absorption capacity=Weight of superabsorbent (g) in sample·Free swell capacity in synthetic urine+Weight pulp fibers (g)·Absorption capacity of pulp.

The absorption capacity for pulp fibers were measured after 60 minutes of free absorption in synthetic urine to be 8 g urine/g pulp.

Free swell capacity for the superabsorbent was measured by the below described method.

The result is shown in the diagrams in FIGS. 1a and b, from which it can be seen that the utilization degree at the portions located furthest away from the wetting area were clearly better for the test substances as compared to the reference.

Formula for Synthetic Urine 0.66 g/l magnesium sulphate, 4.47 g/l potassium chloride, 7.60 g/l sodium chloride, 18.00 g/l urea, 3.54 g/l potassium dihydrogen phosphate, 0.745 g/l sodium hydrogen phosphate, 1.00 g/l 0.1-%-ig triton, 0.4 g/l Nykockin (colour), rest de-ionized water.

Free Swell Capacitor

Pouches of polyester net 7×12 cm were prepared. 0.2 g of superabsorbent were weighed and placed in the pouches, which were welded and weighed. The pouches were immersed in synthetic urine during 60 minutes after which they were taken up, were allowed to drain and were weighed. The difference in weight after and before absorption gives the free swell capacity.

Acquisition Time

Figure 2A:
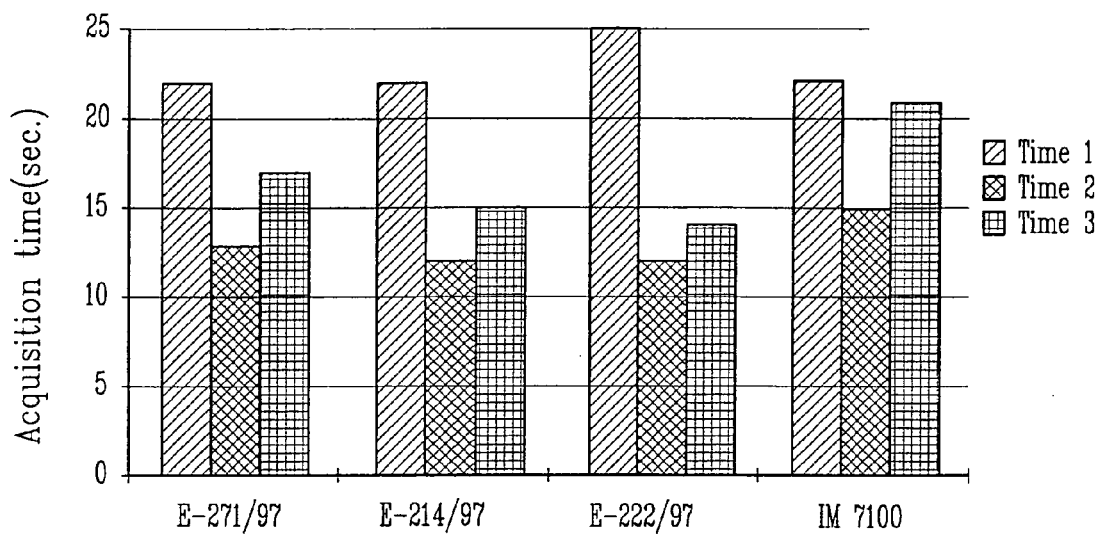
FIGS. 2a and b show in the form of bar charts the acquisition time at the first, second and third wetting occasions in absorbent articles containing different superabsorbents in an amount of 50 and 70% by weight respectively.
Figure 2B:
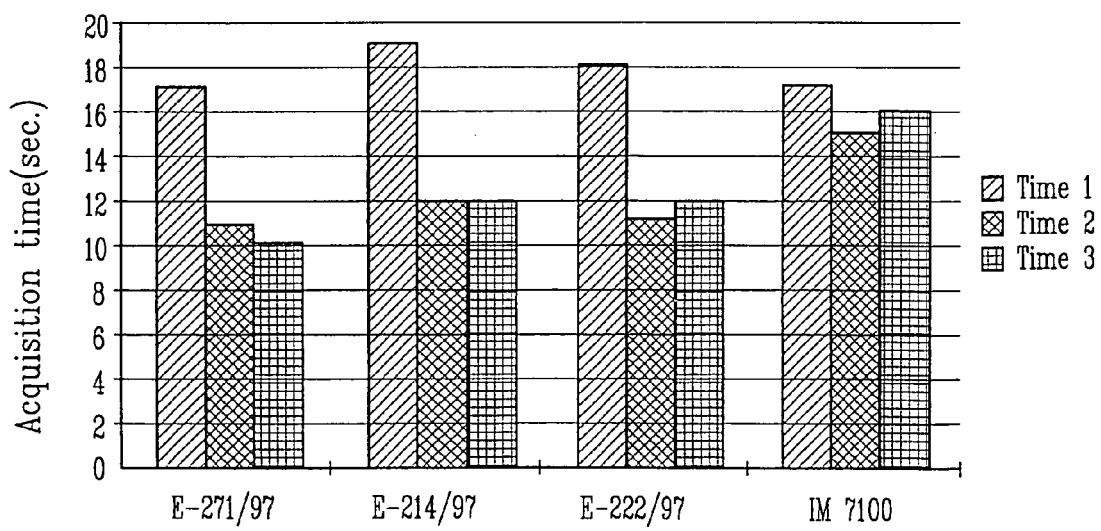

Three additions of each 80 ml synthetic urine were made through a plexiglass tube (inner diameter 23 mm) placed on the test bodies. The time interval between the additions were 10 minutes. The time it took until all liquid was absorbed was measured (visual observation). The result of the measurements is shown in FIGS. 2a and b. It is seen that the acquisition time at the second and especially the third addition was lower for the absorbent bodies containing the test substances as compared to the reference substance.

Rewet

Rewet was measured after 10 minutes after each addition by placing a filter paper on the wetting area and load it with a weight of 2550 g during 15 seconds. The filter paper was weighed before and after the loading and the rewet was calculated.

Figure 3A:
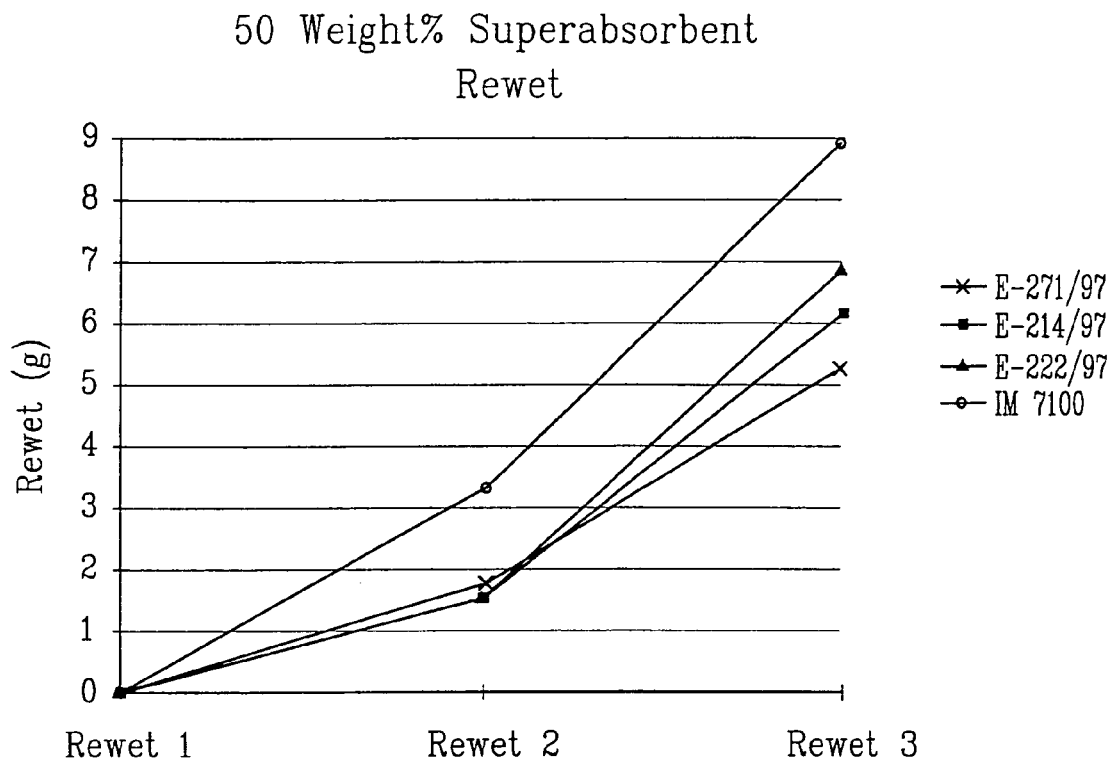
FIGS. 3a and b shows in the form of diagrams the rewet after the first, second and third wetting occasions of absorbent articles containing different superabsorbents in an amount of 50 and 70% by weight respectively.
Figure 3B:
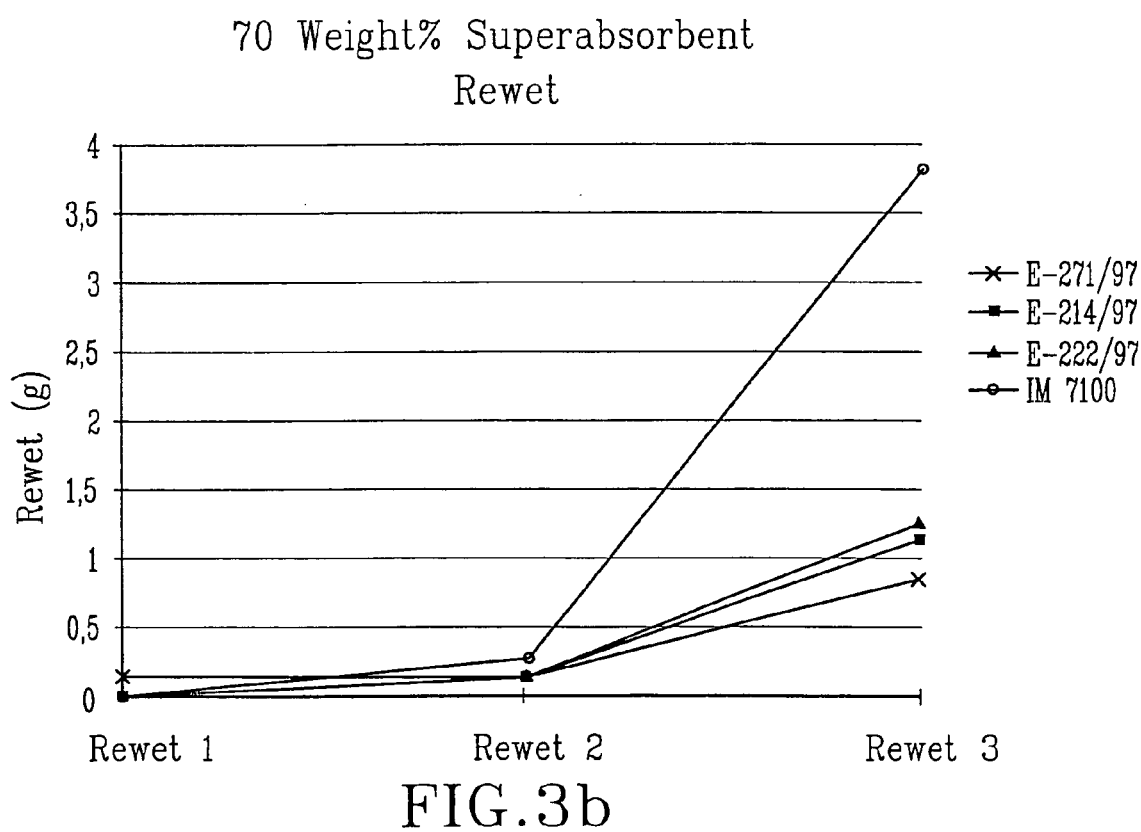

The result is shown in FIGS. 3a and b, at which it can be seen that the rewet after the first wetting occasion was substantially the same and very low both for the absorbent bodies containing test substances and the reference substance respectively. For the absorbent bodies containing 50% superabsorbent (FIG. 1a) there was already after the second addition observed a difference in rewet between the reference body and the test bodies, a difference that reamined also after the third addition. For the absorbent bodies containing 70% superabsorbent (FIG. 3b) the rewet was the same also after the second addition, but after the third addition the difference between the test bodies and the reference body was significant, in such a way that the test bodies had a considerably lower rewet than the reference body.

Momentaneous Acquisition Time Under a Certain Pressure

Figure 4A:
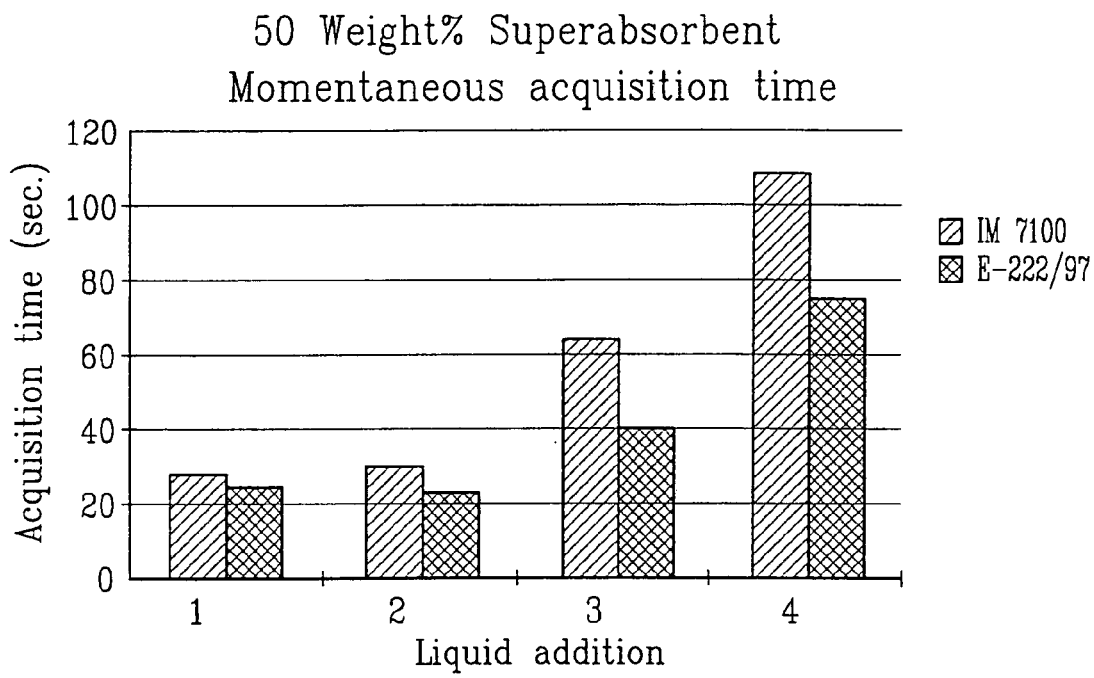
FIGS. 4a and b show in the form of bar charts the momentaneous acquisition time under a certain load at the first, second, third and fourth wetting occasions in absorbent articles containing different superabsorbents with a content of 50 and 70% by weight respectively.
Figure 4B:
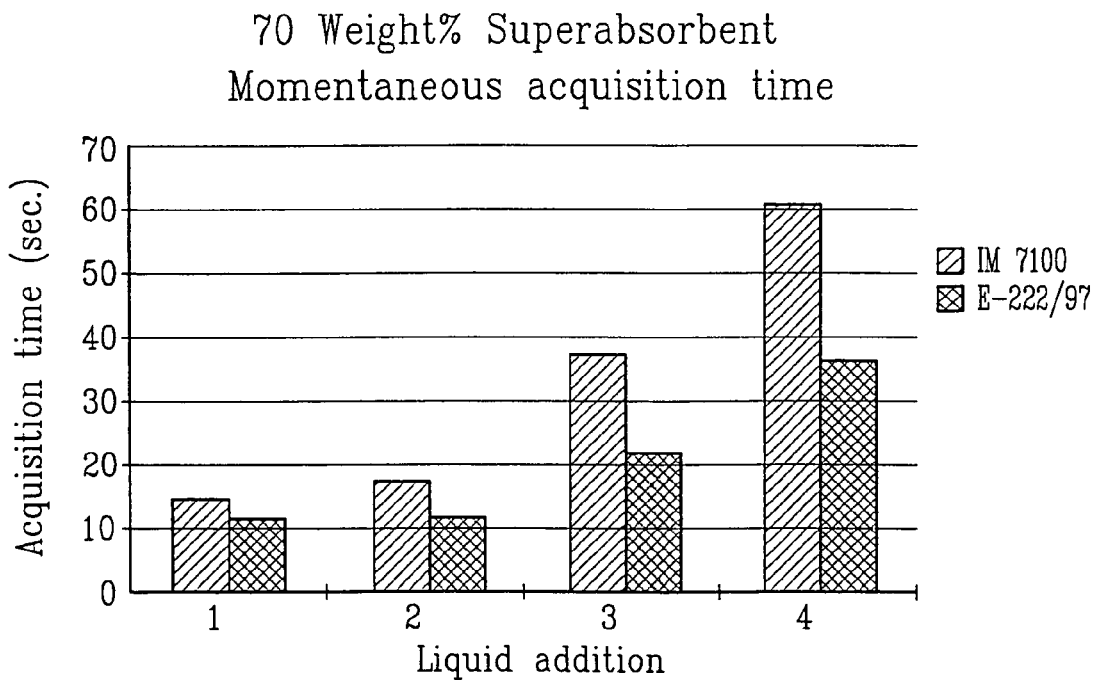

The tested absorbent bodies were clamped under a plexiglass disc, which had a circular opening. Four addition each of 80 ml synthetic urine were made through the circular opening via a funnel and a petri disc. The time interval between the additions were 10 minutes. The time it took until all liquid had been absorbed was measured (visual observation). The result is shown in FIGS. 4a and b. The acquisition time for the test substance (E-222/97) was lower at all additions as compared to the reference substance (IM 7100). The difference was biggest at the third and fourth addition. Similar results were obtained with respect to 50 as well as to 70% by weight superabsorbent.

Besides the shown advantages with respect to improved absorption properties of absorbent structures containing ionically crosslinked superabsorbents the latter have a further important advantage, viz. that they have a higher resistance to mechanical stress that may occur when handling the superabsorbent particles in for example a diaper machine. A superabsorbent particle which is only covalently surface crosslinked and where the surface layer is damaged due to mechanical stress will loose much of its gel stability. A superabsorbent particle which is ionically crosslinked, either homogeneously or only on the surface, will substantially maintain its gel stability even after mechanical damages of parts of the surface layer. In a superabsorbent particle that is ionically surface crosslinked the ionic crosslinking bonds can be redistributed over the particle surface and in such a way repair possible damages in the surface layer.

What is claimed is:

1. An absorbent structure in an absorbent article selected from the group consisting of a diaper, a pant diaper, an incontinence guard, and a sanitary napkin, said structure comprising a combination of a porous material selected from the group consisting of fibers, foam and mixtures thereof, and a superabsorbent material, wherein the absorbent structure contains at least 50% by weight of superabsorbent material, based on the total weight of the structure in dry condition in at least one area thereof in which the superabsorbent material is distributed; said superabsorbent material being in the form of a powder, grains or granules, and being initially crosslinked by ionic bonds with an ionic crosslinking agent comprising an aluminate ion; the superabsorbent material being also covalently cross-linked.

2. The absorbent structure according to claim 1, wherein the superabsorbent material comprises a polymer with anionic functional groups.

3. The absorbent structure according to claim 2, wherein the superabsorbent material is a crosslinked polymer of a polyacrylate having functional carboxy groups.

4. The absorbent structure according to claim 2, wherein the superabsorbent material is crosslinked with a cationic crosslinking agent by cations which are bonded to the anionic functional groups of the superabsorbent material via ionic bonds.

5. The absorbent structure according to claim 4, wherein the cationic crosslinking agent comprises a polyvalent metal ion.

6. The absorbent structure according to claim 1, wherein the superabsorbent material is surface crosslinked by the ionic crosslinking agent.

7. The absorbent structure according to claim 6, wherein the superabsorbent material is substantially homogeneously crosslinked with the ionic crosslinking agent.

8. The absorbent structure according to claim 1, wherein the absorbent structure contains at least 70% by weight of superabsorbent material, calculated on the total weight of the structure in dry condition in at least one area thereof in which the superabsorbent material is distributed.

9. An absorbent article selected from the group consisting of a diaper, a pant diaper, an incontinence guard, and a sanitary napkin, the article comprising a liquid pervious topsheet, a liquid impervious backsheet and an absorbent structure enclosed therebetween; said absorbent structure comprising a combination of a porous material selected from the group consisting of fibers, foam and mixtures thereof, and a superabsorbent material, wherein the absorbent structure contains at least 50% by weight of superabsorbent material, based on the total weight of the structure in dry condition in at least one area thereof in which the superabsorbent material is distributed; said superabsorbent material being in the form of a powder, grains or granules, and being initially crosslinked by ionic bonds with an ionic crosslinking agent comprising an aluminate ion; the superabsorbent material being also covalently cross-linked.

\* \* \* \* \*

UNITED STATES PATENT AND TRADEMARK OFFICE
CERTIFICATE OF CORRECTION

PATENT NO. : 6,930,221 B1
DATED : August 16, 2005
INVENTOR(S) : Strandqvist

It is certified that error appears in the above-identified patent and that said Letters Patent is hereby corrected as shown below:

<u>Title page,</u>
Item [56], References Cited, add
-- FOREIGN PATENT DOCUMENTS
WO          WO 93/25735         12/1993
WO          WO 94/25519         11/1994 --.

Signed and Sealed this

Twenty-first Day of March, 2006

JON W. DUDAS
*Director of the United States Patent and Trademark Office*